(12) United States Patent
Watkins et al.

(10) Patent No.: US 7,703,332 B2
(45) Date of Patent: Apr. 27, 2010

(54) TENSILE TESTER

(76) Inventors: Penelope Ann Watkins, Syrusa, St. Nicholas Close, Gayton, Norfolk (GB) PE32 1QS; Glyn Watkins, Syrusa, St. Nicolas Close, Gayton, Norfolk (GB) PE32 1QS ( * ) Notice: Subject to any disclaimer, the term of this patent is extended or adjusted under 35 U.S.C. 154(b) by 81 days.

(21) Appl. No.: 12/064,500

(22) PCT Filed: Aug. 30, 2006

(86) PCT No.: PCT/GB2006/003210
§ 371 (c)(1),
(2), (4) Date: Feb. 22, 2008

(87) PCT Pub. No.: WO2007/026143
PCT Pub. Date: Mar. 8, 2007

(65) Prior Publication Data
US 2008/0229843 A1   Sep. 25, 2008

(51) Int. Cl.
*G01N 3/08* (2006.01)
(52) U.S. Cl. .............. 73/826; 73/159; 73/160
(58) Field of Classification Search .......... 73/826, 73/862.453, 862.392–862.393, 159–160
See application file for complete search history.

(56) References Cited
U.S. PATENT DOCUMENTS

| | | | | |
|---|---|---|---|---|
| 4,825,702 A | * | 5/1989 | Cizek | 73/828 |
| 4,833,927 A | * | 5/1989 | Park | 73/862.451 |
| 5,603,462 A | * | 2/1997 | Conrad et al. | 242/554.2 |
| 5,628,472 A | * | 5/1997 | Sbalchiero et al. | 242/433.3 |
| 6,095,449 A | * | 8/2000 | Gallo et al. | 242/365.4 |
| 6,487,902 B1 | | 12/2002 | Ghosh | |
| 6,536,087 B2 | * | 3/2003 | Stuttem | 28/248 |
| 6,860,156 B1 | | 3/2005 | Cavallaro et al. | |

FOREIGN PATENT DOCUMENTS

| | | |
|---|---|---|
| EP | 0253644 A2 | 1/1988 |
| EP | 0429376 A1 | 5/1991 |
| GB | 2289068 A | 11/1995 |
| GB | 2323930 A | 10/1998 |

* cited by examiner

*Primary Examiner*—Max Noori
(74) *Attorney, Agent, or Firm*—David A. Guerra

(57) ABSTRACT

The invention provides a tensile tester, for characterising the extension properties of a fabric, comprising: a plurality of dual-mode fabric-engaging units located at a plurality of points. The fabric-engaging units are operable in a first fabric-gripping mode to releasably grip a fabric to be tested, and in a second fabric-tensioning mode to impart tension to a fabric to be tested, between gripped points, by displacing the fabric. The tester also has force measurement means to measure the tension so imparted and displacement measuring means to measure the displacement of the fabric. The fabric-engaging units are arranged and controlled so as to measure displacement-force characteristics along two or more axes of the fabric to be tested. Embodiments of the invention allow for determination of stretch characteristics in the Course, Wale, and two Bias directions of a fabric, as well as the characterisation of tension decay.

19 Claims, 4 Drawing Sheets

Wale measurement

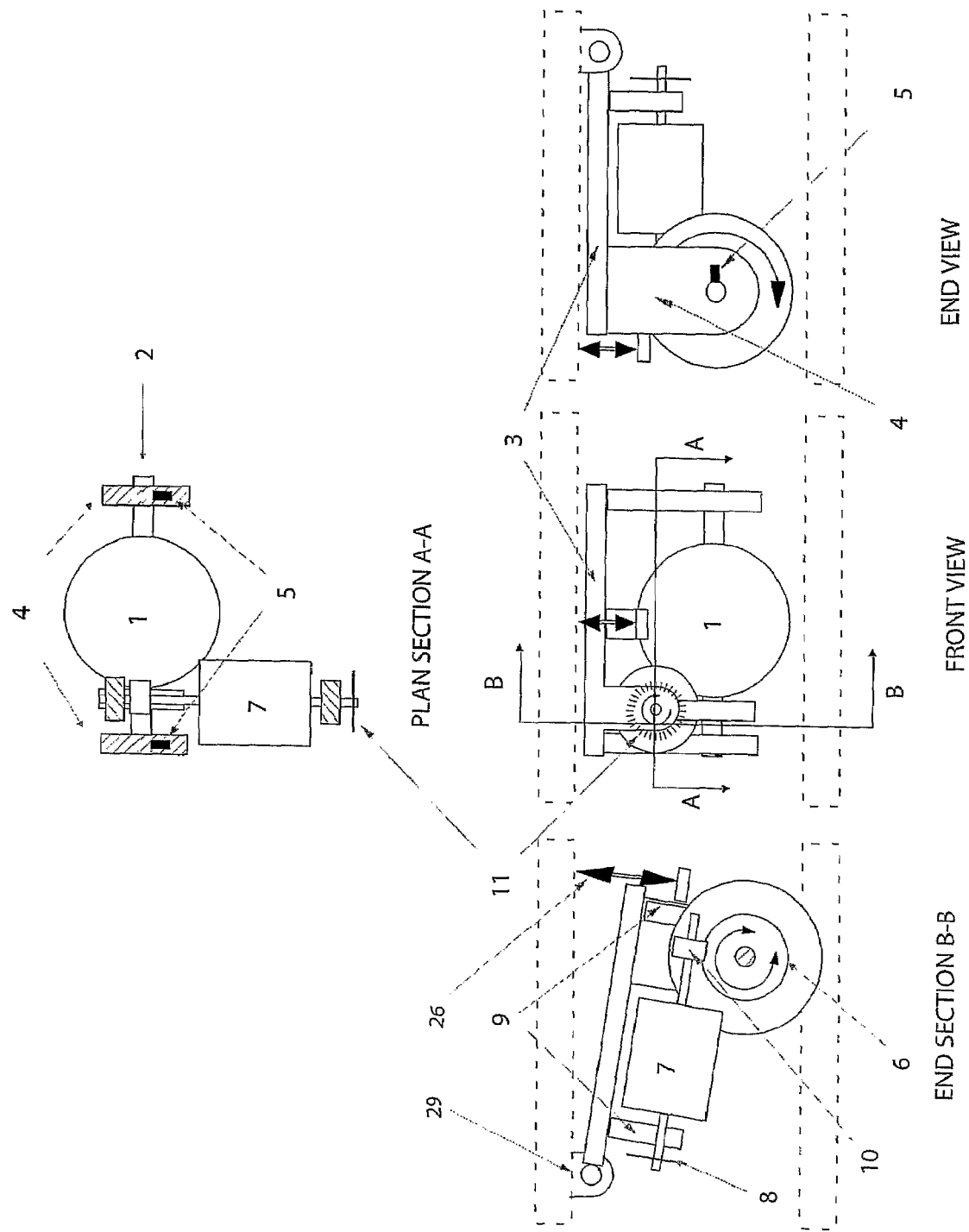
FIG 1 - HEAD ASSEMBLY

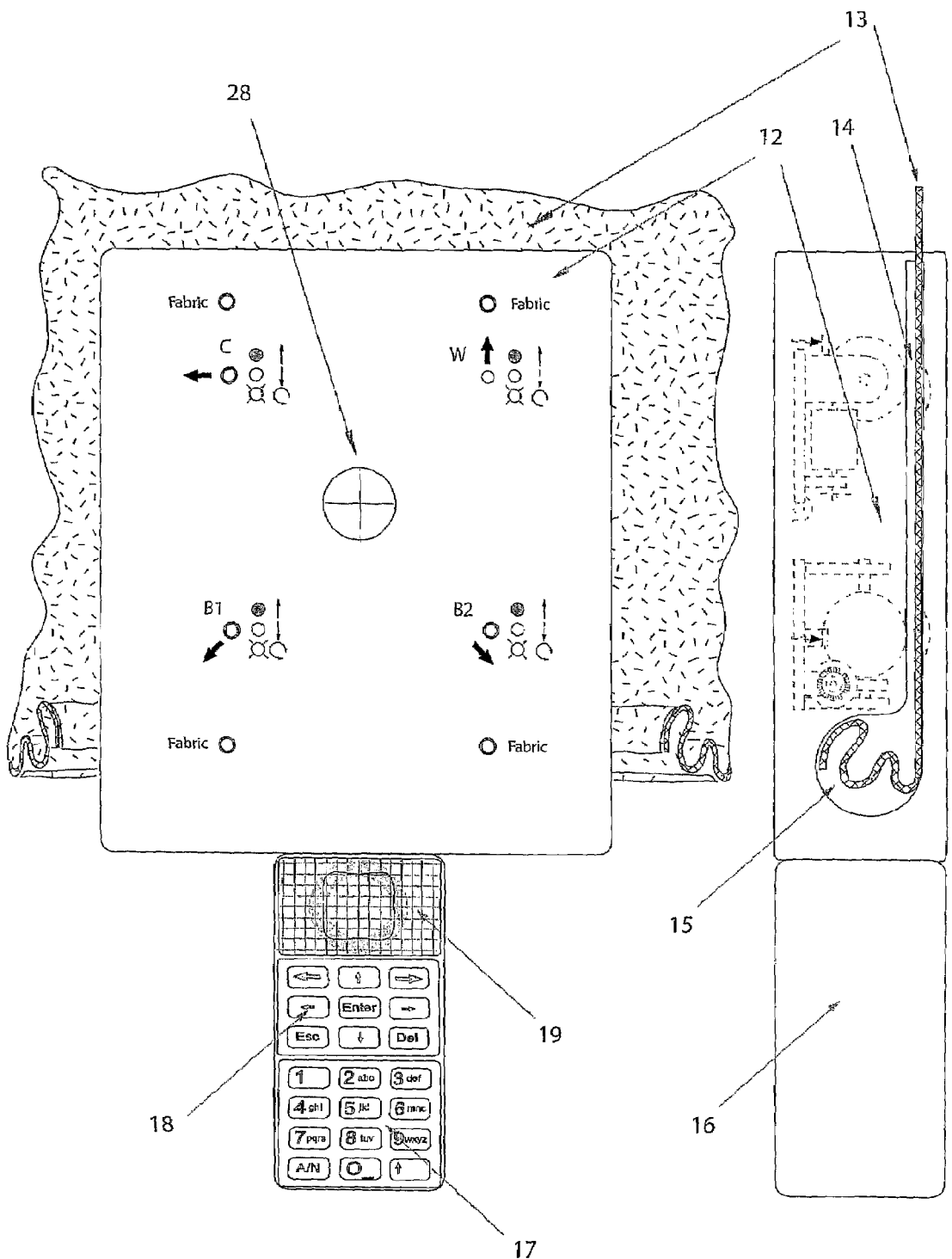
FIG 2 - EXTERNAL VIEW

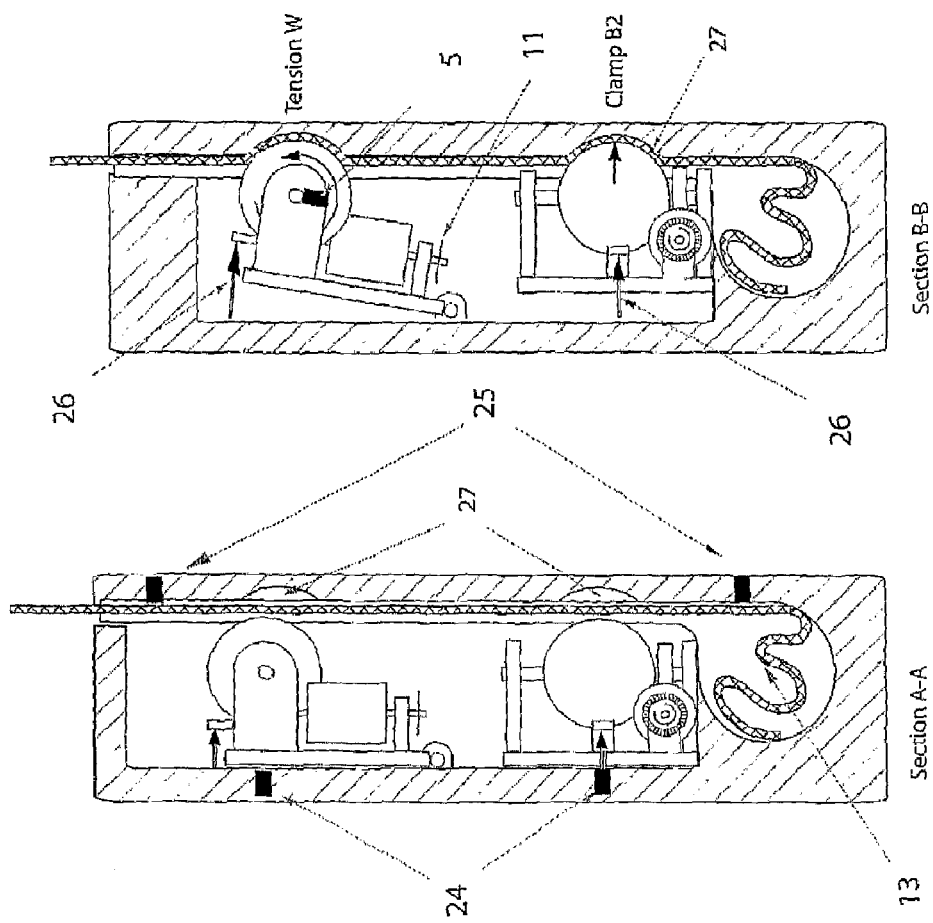
FIG 5 - Wale measurement
FIG 4 - Fabric alignment with heads lifted.
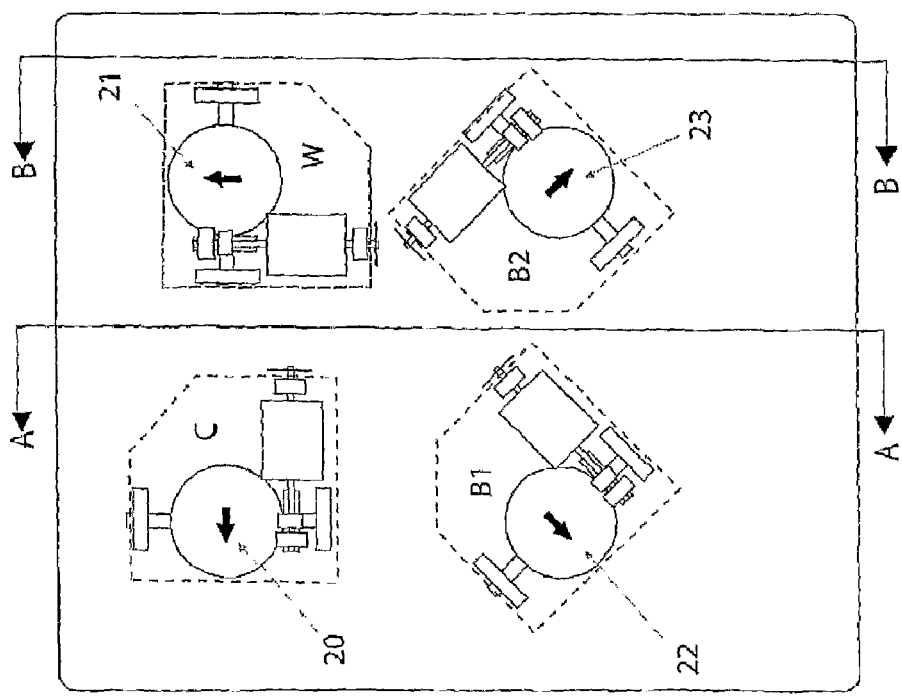
FIG 3 - Head orientation

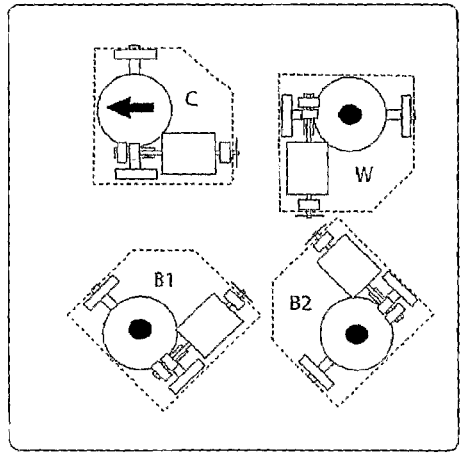
Course - Tension C
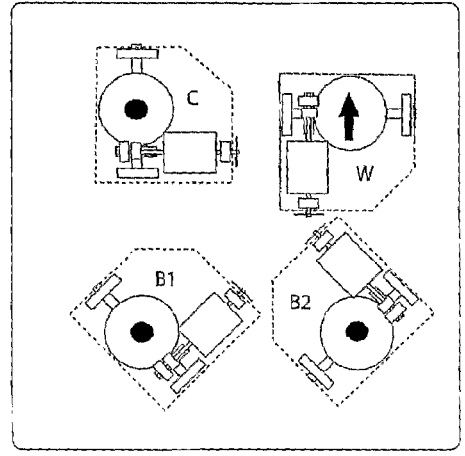
Wale - Tension W
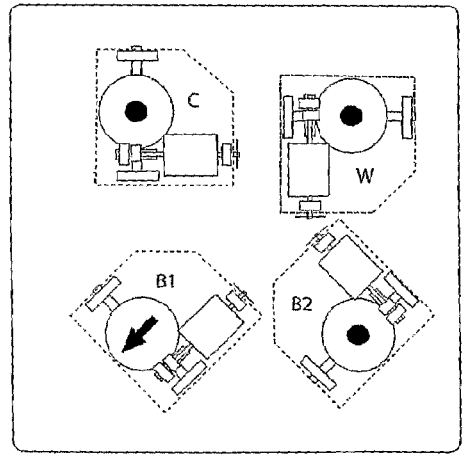
Bias 1 - Tension B1
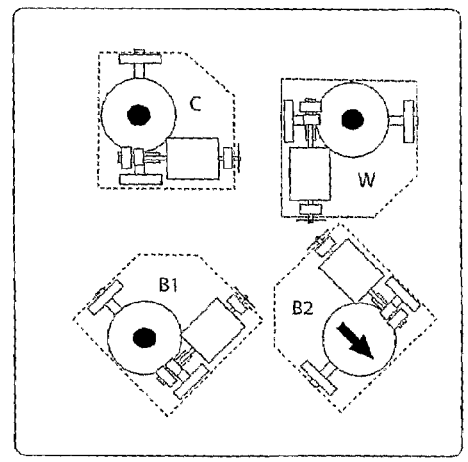
Bias 2 - Tension B2
FIG 6 - MEASUREMENT SEQUENCE

TENSILE TESTER

CROSS-REFERENCE TO RELATED APPLICATIONS

This application is an U.S. national phase application under 35 U.S.C. §371 based upon co-pending International Application No. PCT/GB2006/003210 filed on Aug. 30, 2006. Additionally, this U.S. national phase application claims the benefit of priority of co-pending International Application No. PCT/GB2006/003210 filed on Aug. 30, 2006 and Great Britain Application No. 0517659.9 filed on Aug. 31, 2005. The entire disclosures of the prior applications are incorporated herein by reference. The international application was published on Mar. 8, 2007 under Publication No. WO 2007/026143 A1.

FIELD OF THE INVENTION

The invention relates to instruments for characterising the extension properties of planar materials having a low modulus of elasticity such as stretch fabrics and stretch fabrics containing elastane.

BACKGROUND AND PRIOR ART KNOWN TO THE APPLICANT

Demand for stretch garments, which apply varying degrees of compressive stretch for sportswear, cosmetic body shaping and medical applications is increasing. In evolutionary terms stretch garment pattern design is in its infancy. Pattern drafting techniques for woven block patterns are well established. Applying these techniques to generate patterns for stretch fabrics can be successful, but it is often at a cost. Using the simplified shapes of modified traditional patterns, proportionately reduced by an arbitrary amount or using smaller sized patterns, can generate garments of dubious fit. All conventional pattern-drafting techniques are based on mathematical formulae that have evolved encompassing an implicit fit rationale. How companies arrived at their approximation of the ideal pattern profile for their particular demographic fit model is usually dependent on the subjectivity and expertise of the designer/technologist fitter. Currently determining the degree of fabric extension and how to apply the amount of available stretch in the pattern reduction process is subjective. Traditional approaches to pattern geometry combined with an arbitrary degree of stretch extension introduces variables at each stage, thus impeding objectivity and the technological evolution of stretch pattern profiling.

Stretch fabrics are produced in a broad range of fibre content and weights with a stretch extension capacity for a variety of applications. Manufacturers of stretch fabric normally use laboratory based electronic testing instruments for the climatically controlled measurement of tensile characteristics. British and American Standard Tests include methods for: fatiguing or ageing specimens; determining extensions at a specific force, modulus, tension decay, residual extension, fatigue set, elastomeric thread break and runback. Fabric and fibre producers and garment technologist use these standard tests to assess the fitness for purpose of a garment fabric and have specific quality assurance parameters in common.

Most manufacturers tend to state a single averaged course/wale stretch for the fabric quality, usually attributed to a range of fabrics but this can be misleading as it is not generally stated that the degree of stretch is obtained by applying differing loads to the individual fabrics This averaged stretch figure is inadequate for stretch pattern design (Ziegert, B. and Keil, G., *Clothing and Textiles Research Journal*, 1988, 6(4), 54-64).

Information on stretch fabric characteristics and the way stretch extension is quantified in the process of constructing a stretch pattern is not straightforward. To quantify the degree of stretch technical publications for garment pattern construction recommend the hand stretch test method, which is generally agreed to mean 'the useful limit of extension'. Theoretically it is the point at which the stretched fabric has reached its maximum extension without deforming the hard yarns or fibres (Murden, 1966:356, Elastomeric Thread Review (II): Elastomeric and Fabric Test Method. *Textile Institute and Industry*, Vol. 4, December, pp. 355-358). Samples of fabric of varying widths different lengths (Haggar, 2004:272, *Pattern Cutting for Lingerie, Beachwear and Leisurewear.* $2^{nd}$ Ed., Oxford: BSP Professional Books; Armstrong, H., 1995, *Patternmaking for Fashion Design*, $2^{nd}$ Ed., Harper Collins, 471, Murden 1966:356) are pulled until a reasonable resistance to stretch is felt, or until they are visually unacceptable. The degree of extension is then measured on a rule and categorised as low, medium or high stretch. This method of assessing fabric stretch extension is also difficult for the designer/technologist to apply objectively in stretch garment design.

Having first recognised the shortcomings of the present technologies, the problem is to establish a qualitative procedure for measuring, recording and specifying fabric characteristics that would be accessible throughout the clothing and allied industries. This would include fabric manufacturers and distributors, designers/pattern technologists, clothing and allied trades manufacturers and retailers.

SUMMARY OF THE INVENTION

Accordingly, the invention provides a tensile tester, for characterising the extension properties of a fabric, comprising: a plurality of dual-mode fabric-engaging units located at a plurality of points, said fabric-engaging units operable in a first fabric-gripping mode to releasably grip a fabric to be tested, and in a second fabric-tensioning mode to impart tension to a fabric to be tested, between gripped points, by displacing the fabric; force measurement means to measure the tension so imparted; displacement measuring means to measure the displacement of the fabric; and wherein the fabric-engaging units are arranged and controlled so as to measure displacement-force characteristics along two or more axes of the fabric to be tested.

Preferably, the fabric, in use, is tensioned by at least one fabric-engaging unit operating in a fabric-gripping mode whilst a corresponding second fabric-engaging unit operates in a fabric-tensioning mode.

Preferably also, the fabric-engaging units are arranged and controlled so as to measure displacement-force characteristics along four axes oriented substantially at 45 degree intervals. This allows a full characterisation of stretch characteristics in the Course, Wale and two Bias directions.

In any aspect of the invention it is also preferable that tensioning means is provided by the rotation of gripping means relative to the fabric. More preferably, the tensioning and gripping means comprise: a rotatably mounted member; a plate; means to bring said member reversibly into engagement with said plate; and wherein the surface of said member has a higher coefficient of friction, relative to a fabric to be tested, than the surface of the plate. In this way, a fabric to be tested is gripped by the rotatably mounted member, against which it is held by the low-friction plate. The fabric slides against the plate whilst being pulled by the rotatably driven member. More preferably still, the plate has an indent shaped so as to engage with a portion of said member; and wherein the surface of said member has a higher coefficient of friction, relative to a fabric to be tested, than the surface of the indent. The provision of the inter-engaging feature increases the grip on the fabric, and prevents slippage. With or without the indent feature, the member is substantially spherical. The use of a spherical member reduces edge effects that might be produced with e.g. a cylindrical member.

In any aspect of the invention, it is preferable that the tensile tester according further comprises timing means and processing means to measure tension decay in a fabric to be tested. Tension may be applied to a fabric by pulling it between gripping points, and the reduction of tension over time measured as the fabric relaxes.

Included within the scope of the invention is a tensile tester substantially as described herein, with reference to and as illustrated by any appropriate combination of the accompanying drawings.

The invention provides a compact, portable testing instrument that measures the degree of extension of planar materials having a low modulus of elasticity such as stretch fabrics, more specifically stretch fabrics containing elastane, hereafter referred to as fabric. The measurement procedure need not be invasive in as much as a sample of standard dimensions does not necessarily have to be prepared. Measurement can be taken on a portion of fabric that may form part of a roll of fabric, a made-up garment or a cut sample.

One aspect of the invention is the measuring and recording of the low modulus stretch characteristics of the fabric in four directions of 45 degrees orientation, referred to as course, wale, bias 1 and bias 2.

In a particularly preferred embodiment of the invention, a unique feature is the clamping arrangement. The fabric is clamped between spherical balls and corresponding depressions (indents) in the bed of the invention. The balls are preferably manufactured from a material having a high coefficient of friction relative to the fabric, such as a rubber compound. The bed is manufactured from a material with a very low coefficient of friction relative to the fabric, such as ceramic. The bed depression surface area, being a function of the sphere diameter and the depression depth, will affect the frictional force between the fabric and the bed when the ball is rotated. The downward force required to clamp the fabric will be a function of the frictional force between the ball and the fabric and the extent to which the fabric will to be stretched. The fine balancing of these factors will be explained in the following text.

The embodiment has four identical head assemblies statically mounted symmetrically in a square formation. The principal components for a head assembly are a sphere, a drive motor and suitable gearbox for the required mechanical advantage and an actuator mechanism for lowering and raising the sphere assembly.

To measure the stretch in a given orientation initially at least two of the four heads are lowered to clamp the fabric, followed by the rotation of a selected head in a direction such as to apply tension to the fabric. The angular rotation of the ball and the force required to stretch the fabric is be monitored and recorded from which force/extension data can be derived. Because each head can operate either as a static head applying a downward force to grip the fabric or a dynamic head applying torque in order to stretch the fabric, the selection of such suitable materials, the forces involved and the dimensions of scale are important.

FIG. 1 shows the various views of the head assembly. A sphere 1 is mounted on the sphere shaft 2, which is attached to head assembly top plate 3 by two sphere mounting pillars 4 each fitted with tension load transducers 5. A sphere drive cog 6 is fitted to the sphere shaft. A motor 7 drives the motor shaft 8, which is also attached to the head assembly top plate 3 by two motor mounting pillars 9. A motor drive cog 10 in contact with the sphere drive cog 6, form a gearbox. A digitiser 11 is fitted to the motor shaft. The head assemble has a pivot 29 allowing the head assembly to be raised and lowered by the head actuator mechanism 26.

FIG. 2 is an external view of the invention. The head housing 12 contains four head assemblies, the position and functionality being described below. The fabric to be tested 13 is inserted into the slot 14. Excess material such as the seams, welts and hems of garments or fabric selvedge is accommodated in the excess fabric chamber 15. Suitable location of the electronics can be ascertained by routine development; by way of example, the handhold 16 for the invention could contain an alphanumeric keypad 17, menu navigational keys 18 and a liquid crystal display 19. Enclosed within the handhold could be a mains/battery power source, a microprocessor controlled printed circuit board with analogue and digital interfaced controlling the invention and standard interfaces for mains input and bi-directional data transfer, wired or wireless. Basic visual indication could be provided on the face of the invention for the presence of fabric and the sequencing of each head. This type of functionality would be well known to experts in this field. To enable an operator to correctly position a fabric sample, fabric alignment and structural identification is provided for by a backlit magnifier 28 incorporating horizontal and vertical axis indication.

FIG. 3 is a sectional plan view of the invention illustrating the positioning and orientation of the four heads contained within, which are identified as the C head 20, the W head 21, the B1 head 22 and the B2 head 23, corresponding to course, wale, bias 1 and bias 2 respectively.

FIG. 4 is a sectional view of head housing. All four heads may be separated from their corresponding indents by the head actuators 26, and detected by the head raised sensors 24, prior to inserting the fabric 13. When the fabric is inserted, fabric sensors 25 will confirm the correct positioning of the fabric.

FIG. 5, by way of example, illustrates the starting procedure for a measurement in the wale direction whereby, after the fabric has been detected, all four heads are lowered by the head actuators mechanism 26, forming static clamps between the head and the base plate depression 27. The actuator mechanisms would preferably be pre-calibrated for the range of fabrics to be tested. The wale head 21 will then rotated, bringing the fabric under tension. The tension load cell 5 and the corresponding motor digitiser 11 will be used to compute the load/extension curve over the required range. On completion the wale head 20 will be reversed in direction, returning the fabric to its initial position.

FIG. 6 is a plan view showing the clamping sequence for all four directions of stretch whereby, for example, the course stretch is derived by clamping all four heads, as depicted by the black dots, and tensioning the course head 19 in the direction of the arrow.

The present invention has been described in operation when lowering all four heads and rotating a selected head. In order calibrate the tester against known tensile measurements, computer algorithms may readily be developed to produce a high correlation between the test results and comparable laboratory standards. By way of exemplification, the following series of tests is suggested:

In the first instance the invention would be used to measure the degree of extension of samples prepared for standard testing. This would be achieved by manually orientating a prepared sample under the appropriate two heads followed by performing a unidirectional test. The procedure would be repeated for all four orientations thus establishing a correlation between the invention test results and the laboratory standard. This will be referred to as the prepared sample test.

In addition to the prepared sample test, the invention would be used to measure the degree of extension of an unprepared piece of fabric for standard testing. This would be achieved by initially inserting the area of fabric to be tested under all four heads. Two corresponding heads would be lowered followed by a test for that orientation. The procedure would be repeated for all four orientations. The fabric would not be realigned between orientations. This will be referred to as the unprepared sample test.

In addition to the unprepared sample test, because of undesirable fabric movement during the test, better results would be realised by manually realigning the fabric between orientations. An improved correlation would then be expected between the unprepared and realigned unprepared sample tests, so defined In addition to the preceding tests, because the heads may be independently clamped and rotated, it would be possible to automatically realign the fabric between orientations. In a device with limited directional control, however, accurate repositioning would not be possible. The results however would enable the correlations between previous tests to be established. This will be referred to as the unprepared automatically realigned sample test.

In addition to the preceding tests the invention would be used to carry the tests as described in the initial main body of the text whereby all four heads were lowered followed by the rotation of each orientation head in turn. Comprehensive correlation data would then be available for analysis. This will be referred to as the four head sample test.

The preferred test procedure would be the unprepared automatically realigned sample test because the forces required for such a test, and thus the scale of size of the invention, would be lower than the four head sample test. The computed load/extension algorithms for the latter would also be more complex with the possibility of relatively poorer results. Analysis of the final two tests would establish which of the two would be proposed as the one most suitable for the quad testing of stretch fabrics.

In addition, because the four derived values for stretch in the course, wale, bias 1 and bias 2 orientations of the fabric are a direct derivative of the computed algorithms then the results obtained through the use of the invention become a feature of the invention.

The use of such results would enable the establishment of a qualitative procedure for measuring, recording and specifying fabric characteristics that would be accessible throughout the clothing and allied industries. More specifically the modulus, which is the force versus extension, would be used to quantify the fabric stretch, which, for a given force is the extension over the original length. This would assist in communication over the modulus specification for garment requirements between fabric technologists and designer/garment technologists concerned with the degree of fabric stretch extension for pattern reduction. Additional beneficiaries would include fabric manufacturers and distributors, clothing and allied trades manufacturers and retailers.

In addition to the first aspect of the invention, which is the measuring and recording of the low modulus stretch characteristics of fabrics, the invention can be used to simulate additional standard testing procedures for stretch fabrics or assembled garments.

One example of using the invention is for the determination of tension decay whereby the fabric or garment is be stretched to a specified elongation for a given duration and the tension recorded. The extension may be maintained and, by provision of a timer and processing means, the tension decay during this period would be monitored. More specifically the invention may be used to monitor the tension decay in pressure/form-persuasive garments brought about over time.

In addition the invention may be used to determine fabric/garment degradation in use brought about, for example, by the effect of chlorinated water on swimwear, or through contact with atopical substances, medical or otherwise.

Another use for the invention is in the determination of the residual extension of a fabric, whereby the fabric does not fully retract to the pre-stretched measurement. In general the invention would be used to ascertain the suitability of the fabric for the envisaged garment pattern design/production process. For example, the invention may be used to monitor the residual extension in form persuasive garments brought about, for example, through wear, laundering and time.

The invention claimed is:

1. A tensile tester for determining the extension properties of a fabric, said tensile tester comprising:
   a plurality of dual-mode fabric-engaging units located at a plurality of points, said fabric-engaging units operable in a first fabric-gripping mode to releasably grip a fabric to be tested, and in a second fabric-tensioning mode to impart tension to a fabric to be tested, between gripped points, by displacing the fabric;
   force measurement means to measure the tension so imparted on the fabric; and
   displacement measuring means to measure the displacement of the fabric;
   wherein said fabric-engaging units are arranged and controlled so as to measure displacement-force characteristics along at least two axes of the fabric to be tested;
   wherein said fabric-tensioning mode is effected by rotation of gripping means relative to the fabric.

2. The tensile tester according to claim 1, wherein the fabric in use is tensioned by at least one fabric-engaging unit operating in said fabric-gripping mode whilst a corresponding second fabric-engaging unit operates in said fabric-tensioning mode.

3. The tensile tester according to claim 2, wherein said fabric-engaging units are arranged and controlled so as to measure displacement-force characteristics along four axes oriented substantially at 45 degree intervals.

4. The tensile tester according to claim 3, wherein said fabric-engaging units are arranged and controlled so as to allow a full characterization of stretch characteristics in the Course, Wale and two Bias directions.

5. The tensile tester according to claim 1 wherein each of said fabric-engaging units further comprising a rotatably mounted member, a plate, and means to bring said member reversibly into engagement with said plate, wherein the surface of said member has a higher coefficient of friction, relative to the fabric to be tested, than the surface of said plate.

6. The tensile tester according to claim 5, wherein said plate of said fabric-engaging units has an indent shaped so as to engage with a portion of said member, and wherein the surface of said member has a higher coefficient of friction, relative to the fabric to be tested, than the surface of said indent.

7. The tensile tester according to claim 6, wherein said member is a sphere having a substantially spherical configuration.

8. The tensile tester according to claim 7, wherein each of said fabric-engaging units further comprising a sphere shaft mountable to said sphere and attachable to said plate by two sphere mounting pillars, a sphere drive cog fitted to said sphere shaft, a motor attachable to said plate, a motor drive cog in contact with said sphere drive cog, and a digitizer fitted to a motor shaft, said fabric-engaging unit having a pivot allowing said fabric-engaging unit to be raised and lowered by an actuator mechanism, and wherein each of said sphere mounting pillars being fitted with a tension load transducer.

9. The tensile tester according to claim 8, wherein each of said fabric-engaging units further comprising a slot adapted to receive the fabric, and a chamber in communication with said slot for receiving excess fabric.

10. The tensile tester according to claim 9 further comprising timing means and processing means to measure tension decay in the fabric to be tested.

11. The tensile tester according to claim 1 further comprising a handhold and a back-lit magnifier, said handhold having an alphanumeric keypad, menu navigational keys, a liquid crystal display, a microprocessor controlled printed circuit board with analogue and digital interfaced for controlling said tensile tester, and standard interfaces for mains input and bi-directional data transfer, and said back-lit magnifier having horizontal and vertical axis indications so as to enable an operator to correctly position the fabric.

12. A tensile tester comprising:
a housing having a bed defining a slot for receiving a fabric, a chamber in communication with the said slot, and at least two indents defined in said bed and in communication with said slot, said bed being made of a material with a lower coefficient of friction relative to the fabric;
at least two dual-mode fabric-engaging units located at a plurality of points within said housing, said fabric-engaging units operable in a first fabric-gripping mode to releasably grip a fabric to be tested, and in a second fabric-tensioning mode to impart tension to a fabric to be tested, between gripped points, by displacing the fabric, each of said fabric engaging units comprising a sphere mountable to a sphere shaft and attachable to a plate by two sphere mounting pillars, a sphere drive cog fitted to said sphere shaft, a motor attachable to said plate and having a motor shaft, and a motor drive cog in contact with said sphere drive cog, said fabric-engaging units each having a pivot allowing said fabric-engaging unit to be raised and lowered by an actuator mechanism so that said sphere forces the fabric into contact with said indent of said bed;
a tension load transducer fitted to each of said sphere mounting pillars, said tension load transducer being adapted to measure the tension imparted on the fabric; and
a digitizer fitted to said motor shaft of said motor of each of said fabric-engaging units, said digitizer and said tension load transducer being used to compute a load/extension curve over a required range;
wherein said indent of said bed having a shape corresponding to said sphere, and said sphere having a higher coefficient of friction relative to the fabric;
wherein said fabric-engaging units are arranged and controlled so as to measure displacement-force characteristics along at least two axes of the fabric to be tested.

13. The tensile tester according to claim 12, wherein the fabric in use is tensioned by at least one of said at least two fabric-engaging units operating in said fabric-gripping mode whilst the corresponding second fabric-engaging unit operates in said fabric-tensioning mode.

14. The tensile tester according to claim 13, wherein said fabric-engaging units are arranged and controlled so as to measure displacement-force characteristics along four axes oriented substantially at 45 degree intervals.

15. The tensile tester according to claim 14, wherein said fabric-engaging units are arranged and controlled so as to allow a full characterization of stretch characteristics in the Course, Wale and two Bias directions.

16. The tensile tester according to claim 12, wherein said fabric-tensioning mode is effected by rotation of gripping means relative to the fabric.

17. The tensile tester according to claim 12 further comprising timing means and processing means to measure tension decay in the fabric to be tested.

18. The tensile tester according to claim 12 further comprising a handhold and a back-lit magnifier, said handhold having an alphanumeric keypad, menu navigational keys, a liquid crystal display, a microprocessor controlled printed circuit board with analogue and digital interfaced for controlling said tensile tester, and standard interfaces for mains input and bi-directional data transfer, and said back-lit magnifier having horizontal and vertical axis indications so as to enable an operator to correctly position the fabric.

19. A method of using a tensile tester for determining the extension properties of a fabric, said method comprising the steps of:
(a) providing a tensile tester comprising: a plurality of dual-mode fabric-engaging units located at a plurality of points, said fabric-engaging units operable in a first fabric-gripping mode to releasably grip a fabric to be tested, and in a second fabric-tensioning mode to impart tension to a fabric to be tested, between gripped points, by displacing the fabric; force measurement means to measure the tension so imparted on the fabric; and displacement measuring means to measure the displacement of the fabric; wherein said fabric-engaging units are arranged and controlled so as to measure displacement-force characteristics along at least two axes of the fabric to be tested; wherein said fabric-tensioning mode is effected by rotation of gripping means relative to the fabric:
(b) placing the fabric to be tested in said tensile tester;
(c) lowering at least two of said fabric-engaging units to come in contact with the fabric;
(d) clamping the fabric statically using at least one of said at least two fabric-engaging units;
(e) rotating angularly the remaining fabric-engaging unit in a direction such as to apply tension to the fabric;
(f) monitoring and recording said angular rotation of said fabric-engaging units required to stretch the fabric;
(g) deriving force/extension data from said monitored angular rotation; and
(h) reversing the rotation of said fabric-engaging unit in step (e) so as to return the fabric to its initial position before step (e).

* * * * *